US00PP10034P

United States Patent [19]

Lamb et al.

[11] Patent Number: Plant 10,034

[45] Date of Patent: Sep. 16, 1997

[54] ANTHURIUM PLANT NAMED KRYPTON

[75] Inventors: Ann E. Lamb, Sebring; Robert D. Hartman, Lake Placid, both of Fla.

[73] Assignee: Twyford International, Inc., Santa Paula, Calif.

[21] Appl. No.: 629,791

[22] Filed: Apr. 9, 1996

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Foley & Lardner

[57] ABSTRACT

An Anthurium plant named 'Krypton' having small, heart shaped purple spathes with a purple spadix, with the spathes being carried above and among the foliage. The leaves are small, dark green and very shiny. The plant has a miniature growth habit, is highly branched, and is suitable for smaller pot sizes (10 cm). The plant grows to a marketable size and begins flowering quickly.

1 Drawing Sheet

The present invention comprises a new and distinct cultivar of Anthurium, botanically known as *Anthurium hybrid*, and referred to by the cultivar name 'Krypton'.

The new cultivar is a product of a breeding program carried out by the inventors Ann E. Lamb and Robert D. Hartman in Apopka and Sebring, Fla., and is the result of the following cross made in Apopka in February 1993:

| |
|---|
| An unnamed Anthurium hybrid identified by a proprietary code number. |
| × |
| Anthurium '94–4', disclosed in Plant Patent No. 8,820. |

The cultivar was discovered from the progeny of the stated cross in May 1995 by Ann E. Lamb. Tissue culture performed by or under the supervision of Ann E. Lamb at Sebring, Fla. was used to increase the number of plants for evaluation and has demonstrated the stability of the combination of characteristics of 'Krypton' from generation to generation.

The following observations, measurements and values describe plants grown in Homestead, Fla. under shade house conditions which closely approximate those generally used in horticulture practice.

The following traits have been repeatedly observed to be characteristics which in combination distinguish 'Krypton' from other Anthuriums of the same general type, for example, the patented cultivar 'Lady Jane' to which comparative reference is made.

1. The plant produces many small purple spathes, with a purple spadix, with the spathes being carried slightly above and among the foliage.

2. The leaves are small, very dark green, leathery, and shiny.

3. The growth habit is highly branched and compact, making 'Krypton' suitable for smaller pot sizes.

4. The plant grows to a marketable size and begins flowering comparatively quickly.

Compared to 'Lady Jane', 'Krypton' has a compact, highly branched, miniature growth habit. In addition, inflorescences of 'Krypton' are dark purple, numerous, and smaller than those of 'Lady Jane'.

All color references are measured against The Royal Horticultural Society color chart. Colors are approximate as color depends on horticultural practices such as light level and fertilization rate, among others, without, however, any variance in genotype.

The color photographic drawing comprises a top perspective view of the inflorescence and foliage of a plant of 'Krypton' in a 15.3 cm pot approximately 10 months after planting a 20 week old liner obtained by tissue culture and grown under appropriate growing conditions. Colors are as accurate as possible with color illustrations of this type.

Origin: Seedling selected from a cross of an unnamed Anthurium hybrid identified by a proprietary code number × Anthurium '94–42'.

Classification: *Anthurium hybrid*, cv. 'Krypton'.

Propagation: Asexual production either by tissue culture or division.

Inflorescence

Immature: The spathe is tightly rolled around the spadix and emerges from the petiole sheath. The spathe is fully open about when the peduncle is fully elongated, approximately 18 cm to 19.8 cm above the soil surface. The color of the flower peduncle is 146 A flushed with 175 A.

Mature:

*Color.*—Fully open: Upper surface: 60 A–B. Lower surface: 59 C–D. Faded: Upper Surface: 185 B–C. Lower Surface: 59 C–D.

*Arrangement.*—The inflorescence terminates from a straight or often curved wiry peduncle and opens vertically among or slightly above the leaf canopy.

*Shape.*—The spathe is heart shaped with a cordate base and a cuspidate tip.

*Size.*—The fully expanded spathe is approximately 3.0 cm to 3.6 cm long and approximately 3.0 cm to 3.4 cm in width.

*Flowering time.*—After approximately 10 months from a 20 week old liner for an untreated plant as illustrated in the photograph and depending on season, approximately 6 to 8 blossoms will be present. Smaller blooms may occur on less mature growth. First flowers have been observed in 20 week old finished liners.

Reproductive organs:

*Spadix: Size: Approximately* 2.7 cm to 3.0 cm in height and approximately 5 mm in width. Color: When the spathe unrolls, the spadix is 84 C at the base, 187 D in the center, and 186 A at the tip. Stamens: Anthers and filaments are minute and not clearly visible. Pollen is white in color. Pistil: Translucent white, protruding between the staminate flowers, firmly fixed to the main axil. The pistilate flowers extend approximately 0.1 mm beyond the staminate flowers.

General Appearance: Under appropriate growing conditions, 'Krypton' reaches a size of approximately 19.5 cm to 25 cm in height and approximately 41 cm to 45 cm in width.

Leaves:

*Form.*—The leaf blade is ovate with an acute tip and a truncate to slightly cordate base. The midrib is straight over the length of the leaf, and often curved downward at the tip. The leaf margins are somewhat wavy. The leaf blade is leathery in texture, with a very shiny surface.

*Size.*—Leaf blades of a mature sized plant are approximately 12 cm to 14.5 cm in length and approximately 6.8 cm to 8.3 cm in width measured at the widest point.

*Veins.*—The veins are sunken, with the leaf blade noticeably convex between veins on the upper surface. The midrib protrudes from the upper surface of the leaf for approximately ⅔ the length of the leaf. Well defined primary veins on leaves radiate out from the junction of the petiole and the leaf. Veins stand out prominently on the lower side. There are approximately 4–6 primary veins on the leaf.

*Petiole.*—The petiole is approximately 15 cm to 18 cm in height from the base of the petiole to the base of the leaf blade on the primary shoot. Secondary shoots are somewhat smaller depending on the age of the shoot. The petiole is approximately 3.2 mm in diameter just below the geniculum. The petiole below the geniculum is straight.

*Petiole wings.*—Petiole wings are approximately 1.7 cm in length and approximately 4.5 mm in width at their midpoint. The tip of the petiole wings is rounded. There is approximately 13.2 cm between the top of the wing and the base of the geniculum.

*Geniculum.*—The geniculum is approximately 2.0 cm in length, approximately 4.0 mm in diameter, and is often curved. There is no space between the top of the geniculum and the base of the leaf blade.

*Lobes.*—The leaf has two lobes which do not extend past the petiole. The distance from the petiole/leaf juncture to the highest point on the lobes is approximately 4.4 cm to 4.7 cm.

*Colors.*—Upper surface: Much darker and greener, but closest to, 147 A. Newly expanded leaves are typically flushed with bronze. Lower surface: 146 B. Midrib, upper surface: 146 B. Midrib, lower surface: 146 C. Petiole: 146 C–D, becoming anthocyanous when exposed to bright light. Petiole wing: 146 D. Geniculum: 146 D.

Roots: White fleshy roots with fine laterals. The roots are 184 A in color when produced above the soil and exposed to light.

We claim:

1. A new and distinct cultivar of Anthurium plant named 'Krypton', as illustrated and described.

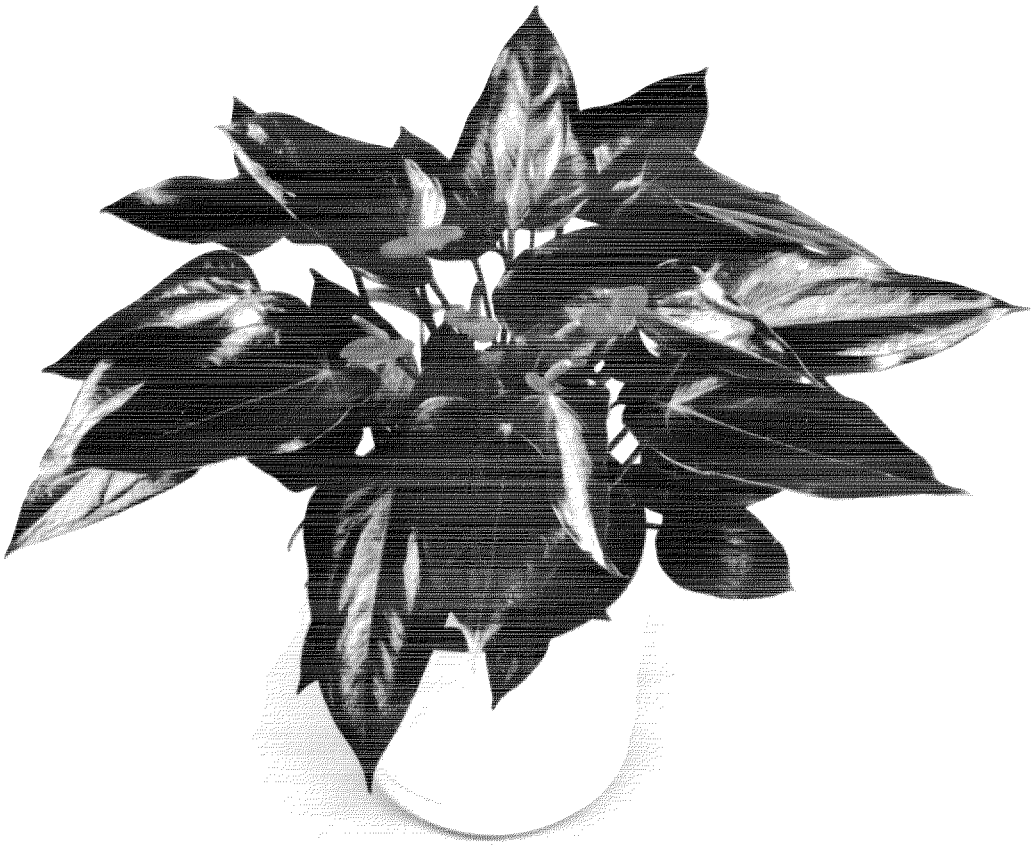

* * * * *